United States Patent
van Eupen et al.

(10) Patent No.: US 7,365,086 B2
(45) Date of Patent: *Apr. 29, 2008

(54) PRAMIPEXOLE ACID ADDITION SALTS

(75) Inventors: Jacobus T. H. van Eupen, Gemert (NL); Frantisek Picha, Brno (CZ)

(73) Assignee: Synthon IP Inc., Gainesville, VA (US)

( * ) Notice: Subject to any disclaimer, the term of this patent is extended or adjusted under 35 U.S.C. 154(b) by 187 days.

This patent is subject to a terminal disclaimer.

(21) Appl. No.: 10/895,996

(22) Filed: Jul. 22, 2004

(65) Prior Publication Data

US 2005/0059717 A1    Mar. 17, 2005

Related U.S. Application Data

(60) Provisional application No. 60/489,922, filed on Jul. 25, 2003.

(51) Int. Cl.
*A61K 31/428* (2006.01)
*C07D 277/82* (2006.01)

(52) U.S. Cl. .................. 514/367; 548/164; 514/367
(58) Field of Classification Search ............... 548/164; 514/367
See application file for complete search history.

(56) References Cited

U.S. PATENT DOCUMENTS

| 4,843,086 | A | 6/1989 | Griss |
| 4,886,812 | A * | 12/1989 | Griss et al. .............. 514/321 |
| 6,727,367 | B2 * | 4/2004 | Pospisilik ................ 548/164 |
| 6,770,761 | B2 | 8/2004 | Pospisilik et al. |

FOREIGN PATENT DOCUMENTS

EP    0 207 696 A    1/1987

OTHER PUBLICATIONS

Kolasiewicz, et al., "Locomotor Hypoactivity and Motor Disturbances—Behavioral Effects Induced By Intracerebellar Microinjections of Dopaminergic DA-D2/D3 Receptor Agonists," Polish Journal of Pharmacology, vol. 53, pp. 509-515 (2001).*

* cited by examiner

*Primary Examiner*—Kamal A Saeed
*Assistant Examiner*—Janet L. Coppins
(74) *Attorney, Agent, or Firm*—Mark R. Buscher

(57) ABSTRACT

The benzene sulfonic acid salts of pramipexole have moderate water solubility and are useful pharmaceutical active agents.

20 Claims, No Drawings

PRAMIPEXOLE ACID ADDITION SALTS

This application claims the benefit of priority under 35 U.S.C. § 119(e) from U.S. provisional application 60/489,922, filed Jul. 25, 2003, the entire contents of which are incorporated herein by reference.

BACKGROUND OF THE INVENTION

The present invention relates to moderately soluble benzene sulfonic acid salts of pramipexole and their use in pharmaceutical compositions and treatments.

Pramipexole, or 2-amino-6-propylamino-4,5,6,7-tetrahydrobenzothiazole, is a known pharmaceutically active agent that has been proposed for treating schizophrenia, Parkinson's disease or Parkinsonism, and/or hypertension (see for example U.S. Pat. No. 4,843,086 and EP 186087). The commercial form of pramipexole has been the dihydrochloride salt of the (S)-enantiomer thereof. The dihydrochloride salt compound is very soluble in water and it is hygroscopic. In solid state, it is generally isolated as a crystalline monohydrate and, indeed, the commercially marketed tablets contain pramipexole dihydrochloride monohydrate. EP 186087 generically teaches the formation of acid addition salts of pramipexole and other similar tetrahydrobenzothiazoles, but only the dihydrochloride salts are exemplified.

Published U.S. patent application No. US 2002-0103240 discloses, inter alia, a process for resolving pramipexole. The process can involve the use of a monobasic salt form of pramipexole as a starting material or intermediate. The monobasic salts, unlike the dihydrochloride salts of EP 186087, have only one acid moiety for each pramipexole. Acids suitable for forming a monobasic salt of pramipexole include hydrochloric, hydrobromic, acetic, benzoic, methane sulfonic, ethane sulfonic, trifluoromethane sulfonic, benzene sulfonic and p-toluene sulfonic acids. Specific examples of monobasic salts include pramipexole monohydrochloride, pramipexole monohydrobromide, pramipexole methanesulfonate, pramipexole trifluoromethanesulfonate, pramipexole p-toluenesulfonate, and pramipexole benzoate. The monobasic salts are primarily taught to be reacted with an optically active acid to form a so-called "mixed salt," which in turn facilitates resolution of the (R) and (S) enantiomers via preferential precipitation.

It would be desirable to have a pharmaceutically acceptable pramipexole salt with more moderate water solubility and/or lower hygroscopicity than the known pramipexole dihydrochloride. Such a salt could provide for better storage stability and/or handling. It would further be desirable to form pramipexole compositions from such a salt. Such formulations may avoid the present need that tablets comprising highly soluble pramipexole salt must,be administered three times a day.

SUMMARY OF THE INVENTION

The present invention relates to the discovery of moderately water-soluble salts of pramipexole. A first aspect of the invention relates to a crystalline benzene sulfonic acid salt of pramipexole. Preferably the solid form is anhydrous, e.g. a crystalline anhydrate. The ratio of benzene sulfonic acid moiety to pramipexole moiety is preferably about 1:1, which is frequently referred to herein as "pramipexole besylate," but is not limited to such a ratio. The salt can be in a substantially pure form and/or isolated form. Preferably the pramipexole is the (S)-isomer, and more preferably has at least 95% optical purity. In terms of optical rotation, the pramipexole besylate preferably exhibits a specific rotation [α] of −49° or less when measured at 20° C. in methanol at the wavelength corresponding to the D line of the sodium emission spectrum.

Another aspect of the invention relates to a pharmaceutical composition comprising a benzene sulfonic acid salt of pramipexole, particularly (S)-pramipexole besylate, and a pharmaceutically acceptable excipient. The pharmaceutical composition is preferably a solid dosage form, especially an oral solid dosage form.

A further aspect of the present invention relates to a method of treating, which comprises administering an effective amount of the pharmaceutical composition comprising a benzene sulfonic acid salt of pramipexole and a pharmaceutically acceptable excipient to a mammal in need thereof. Typically the treatment is for Parkinson's disease or Parkinsonism although other psychotic disorders can be treated as well.

Another aspect of the present invention relates to a process, which comprises precipitating a benzene sulfonic acid salt of pramipexole from a solution containing the same. The precipitation is useful in forming crystalline forms of the salt.

DETAILED DESCRIPTION OF THE INVENTION

The present invention relates to the discovery that benzene sulfonic acid salts of pramipexole generally have low or moderate water solubility. An active agent with extremely high water solubility, such as pramipexole dihydrochloride, can be troublesome in terms of handling, storing, and formulating. For instance, water vapor present in the atmosphere may tend to partially dissolve the active and/or make it wet. These detrimental effects may take place even after the active agent is formulated into a tablet. The wetting of the active can lead to other problems such as interfering with accurate weighing of the active during formulating (e.g. extra water means more water and less active is being supplied to the dosage form) and/or providing a better media for making impurities or degradation products. Pramipexole dihydrochloride monohydrate has a very high water solubility, e.g. approximately greater than 300 mg/ml. To reduce the chance of wetting and the concomitant deleterious effects, it would be desirable to have a pramipexole salt that exhibits a water solubility of 150 mg/ml or less, preferably 100 mg/ml or less. Alternatively, the pramipexole salt should preferably have a water solubility of at least 5 mg/ml, more preferably at least 10 mg/ml, in order to provide good dissolution.

Various pramipexole salts were investigated in an effort to find acceptable water solubility. Surprisingly, most of the pharmaceutically acceptable salts studied had a very high water solubility similar to pramipexole dihydrochloride. The following table summarizes some of the salts studied and their properties.

TABLE 1

Acid Addition Salts of Pramipexole

| Addition Salt of | Melting Point (° C.) | Approximate Water Solubility (mg/ml) | Remarks |
|---|---|---|---|
| Ethane sulfonic acid | 235-236 | >300 | |
| Hexanoic acid | 134-135 | >200 | |

TABLE 1-continued

Acid Addition Salts of Pramipexole

| Addition Salt of | Melting Point (° C.) | Approximate Water Solubility (mg/ml) | Remarks |
|---|---|---|---|
| Pamoic acid | 218 (foaming) | <1 | |
| Tartaric acid | 150 (sintering) | >200 | ⅓ Methanol |
| Tartaric acid | 150 (sintering) | >200 | |
| p-Toluene sulfonic acid | 268-269 | 5 | |
| Methane sulfonic acid | 243-244 | >250 | |
| Methane sulfonic acid | Starts 140 | >250 | Dimesylate |
| Benzoic acid | 163-164 | 125 | ½ Ethanol |
| Sulfuric acid | 288-290 | 53 | |
| Maleic acid | Starts 118 | >250 | |
| Citric acid | 90 foaming | >250 | Ethanol |
| Benzene sulfonic acid | 243-246 | 20 | |

The solubilities listed above are only approximate values. In general the acid addition salt was added to 2 ml of water in a test tube (1 ml of water was used for some of the very soluble salts) until a residue remained. The tube was shaken overnight at room temperature. The next morning 1 ml of the clear solution from above the solid residue was removed from the tube. This sample was evaporated and the residue was dried and weighed. In this way the approximate solubility of the salt in the water was determined. For some of the salts, not enough material was available to reach saturation owing to their high water solubility. Thus the above numbers, especially the numbers over 200, while not quantitatively precise, demonstrate a qualitative difference between various pramipexole salts.

A few of the salts, namely pamoate, tosylate, benzoate, sulfate, and benzene sulfonate, have a much lower water solubility than pramipexole dihydrochloride monohydrate, while most of the tested salts did not. These salts satisfy the desired water solubility criteria and could be used as pharmaceutical active agents in the compositions and processes described below. However, pramipexole benzene sulfonate is the most preferred of the five moderate/low water soluble as the pharmaceutical active agent. Pramipexole pamoate is almost insoluble in water. Pramipexole benzoate appears to favor forming a solvate, in this case ethanolate (see comments in Table 1). Prolonged drying does not remove all of the ethanol from the pramipexole benzoate. Pramipexole sulfate displays extra peaks under differential scanning calorimetry (DSC) analysis, which could indicate polymorphism. Pramipexole toluene sulfonate displays a solubility of approximately 5 mg/ml while pramipexole benzene sulfonate displays a more preferred solubility of approximately 20 mg/ml. Therefore, pramipexole benzene sulfonate, i.e. a benzene sulfonic acid salt of pramipexole, is the most preferred for use as a pharmaceutical active agent.

A benzene sulfonic acid salt of pramipexole is any salt comprising ions of benzene sulfonic acid and pramipexole. The pramipexole can be the (R) or (S) isomer of pramipexole or a mixture of such isomers. Generally the pramipexole salt contains predominantly one isomer, preferably the (S)-isomer of pramipexole. Indeed, this applies to the salts of benzene sulfonic acid as well as any of the other acids as mentioned above. The predominance of the one optical isomer, preferably the (S)-isomer, is such that the pramipexole salt preferably has an optical purity of at least 95%, more preferably at least 98%. In terms of optical rotation, the pramipexole salt preferably exhibits a specific rotation [α] of −49° or less, preferably −50° or less, more preferably −51° or less and still more preferably −52° or less, when measured at 20° C. in methanol at the wavelength corresponding to the D line of the sodium emission spectrum.

The ratio of acid ion to pramipexole ion is generally within the range of 1:1 to 2:1+/−0.2, but is not limited thereto. Preferably the ratio is about 1:1, preferably 1:1 within +/−0.1. Such a salt having about a 1:1 ratio is referred to herein as "pramipexole besylate." The benzene sulfonic acid salts of pramipexole can be in any physical form including solid forms such as crystalline or amorphous forms. Crystalline forms are preferably solvent-free, i.e. anhydrous, meaning that water or other solvent is not bound to the crystal lattice. However, it should be appreciated that even a non-solvate form may contain a solvent, such as water in an anhydrous form, in small amounts typically not more than 1% due to, i.e., insufficient drying, etc.

The benzene sulfonic acid salt of pramipexole can be isolated, i.e. separated from its reaction medium, in solid form with high purity. The product generally exhibits white or substantially white color. Preferably the pramipexole salt is at least 90% pure, more preferably at least 95% pure, still more preferably at least 98% pure. When incorporated into a pharmaceutical composition, as described hereinafter, the benzene sulfonic acid salt of pramipexole is frequently at least 99% pure including at least 99.8% pure.

The most preferred pramipexole salt is pramipexole besylate. In solid state, pramipexole besylate is a stable, preferably crystalline compound, with high melting point. It is moderately soluble in water but has a minimal tendency to absorb water from the environment and in this regard is less hygroscopic than pramipexole dihydrochloride. Water or other solvent, if present in the product after isolation from production, may be easily removed by drying to form a stable, preferably crystalline, anhydrate form. To the contrary, the known pramipexole dihydrochloride does not form a stable anhydrate form. Thus, the preferred pramipexole salt is crystalline pramipexole besylate, more preferably crystalline pramipexole besylate anhydrate, and still more preferably crystalline (S)-pramipexole besylate anhydrate.

The benzene sulfonic acid salts of pramipexole can be formed by a salt forming reaction between a pramipexole moiety and a benzene sulfonic acid moiety. The "pramipexole moiety" can be pramipexole base or a reaction mixture containing, inter alia, pramipexole as a product of chemical transformation, etc. The "benzene sulfonic acid moiety" comprises benzene sulfonic acid, its hydrates and its salts. For making pramipexole besylate it is preferred that the pramipexole moiety be pramipexole base and not a mono-salt of pramipexole as difficulties can be encountered in trying to isolate the pramipexole besylate from a methanol solution thereof.

The salt-forming contact of pramipexole and benzene sulfonic acid moieties proceeds in a solvent that is typically inert to the moieties (does not react with any of the moieties to form side products) and in which the reagents are, at least partly, soluble. The solubility may be enhanced by heating the reaction mixture. Suitable solvents include alcohols, esters, ketones, and mixtures thereof as well as mixtures with water, especially alcohol/water mixtures. The solvents are typically aliphatic and contain 1 to 12 carbon atoms, more typically 1 to 6 carbon atoms.

After the salt has been formed in the solvent, i.e. a solution of a benzene sulfonic acid salt of pramipexole, it is preferred to isolate the pramipexole salt as a solid material. While evaporating off the entire solvent is possible, precipitating the salt is preferred. In this respect, the solvent should also be selected in such a way that the resulting salt is sufficiently insoluble therein and may precipitate therefrom. The insolubility may be enhanced by cooling the solution, removing a part of the solution, or adding a contrasolvent to the solution. A seeding crystal may be added before or during the precipitation. The salt solution forming and precipitation phases may follow each other or they may overlap, in whole or in part. Indeed, the precipitation may occur immediately upon formation of the salt in solution thereby providing simultaneous salt forming and precipitation. Such is included within the present invention so along as the formed salt is at least momentarily dissolved in the solvent before it is precipitated. If the salt forming and precipitation phases are divided, it may be useful to treat the formed solution before precipitation with a suitable adsorption material such as activated charcoal, etc., to remove some impurities present therein.

In suitable solvents, the precipitation force (the difference between solubilities of starting materials and the product) may be so favorable for the salt that the reagents may be used in molar excess, and still only 1:1 salt is precipitated. So either the pramipexole or the benzene sulfonic acid moiety may be used in a certain excess, because the unreacted portion of any of the starting materials remains dissolved and may be removed from the product. Preferably, however, the pramipexole moiety is used in equimolar or excess amounts relative to the benzene sulfonic acid moiety is order to discourage the formation of pramipexole dibesylate; i.e. a 1:2 molar ratio of pramipexole to benzene sulfonic acid.

From the above aspects, the preferred solvent for making the pramipexole besylate is an aliphatic alcohol such as methanol, ethanol or isopropanol.

Isolated pramipexole benzene sulfonates may contain residues of the solvent and thus may be isolated in a hydrated or solvated form. Preferably however, the salt is isolated solvent free; this may be accomplished by careful drying of the product, preferably at diminished pressure. After the product is essentially an anhydrate, i.e. it contains less than 1% of water or other solvent, it is essentially stable against environmental moisture, i.e., it has almost no tendency to absorb water from environment. Thus, the compound may be safely stored at ambient conditions.

The precipitation process may also improve the optical and chemical purity. Using accordingly pure starting material, a compound having at least 95% optical purity and/or at least 95% of chemical purity may be easily obtained. If desired, the product can be recrystallized from a suitable solvent, e.g. from methanol, whereby the purity may be further enhanced. Pure pramipexole besylate has substantially white color.

The pramipexole besylate compound has solid state characteristics that, in some aspects, are superior to the pramipexole dihydrochloride monohydrate:

moderate solubility in water (20 mg/ml)
advantageous pH (as aqueous solution)
stable coloration
non-hygroscopic
high melting point (263-264° C.)
single melting endotherm on DSC (no polymorphic transition)

As used herein, a compound or substance is considered to be non-hygroscopic if it takes on no more than 1 wt %, preferably no more than 0.5 wt %, more preferably no more than 0.2 wt % of water when held at 60% relative humidity (at 25° C.) for 24 hours or until it reaches equilibrium, i.e. no change in weight is occurring, which ever occurs first.

The starting pramipexole base may be prepared by methods known in the art. Particularly, the base may also be prepared from other pramipexole salts, particularly from pramipexole dihydrochloride, by neutralization. The suitable neutralization agent is an organic or inorganic base; preferred solvent for neutralization is water, as the known pramipexole dihydrochloride and also most of the conventional neutralization agents such as alkali metal hydroxides, are very well soluble in water.

Pramipexole base may separate from the solvent as a solid due to the different solubility from the salts. However, it tends to separate as an emulsion. In such a case, the emulsion may be extracted by a water immiscible organic solvent in which the base is sufficiently soluble, such as with chloroform, and the base may be isolated from this solvent, e.g. by evaporation of the solvent.

The benzene sulfonic acid salt of pramipexole can be formulated with a pharmaceutically acceptable excipient or excipients into a pharmaceutical composition. The pharmaceutical compositions of the present invention include the unit dosage form as well as the intermediate bulk formulations such as pellets, beads, powder blends, etc. Typically the composition is a finished dosage form also referred to as a unit dose. Dosage forms include oral dosage forms, topical dosage forms such as a transdermal patch, parenteral dosage forms such as an injectable solution, and rectal dosage forms such as a suppository, but is not limited thereto. Solid dosage forms are normally employed such as tablets, capsules, transdermal patches, etc. Oral dosage forms are the most preferred due to the ease of administration and include solid oral dosage forms such as capsules, tablets, sachets/granules, and powders, as well as liquid oral dosage forms such as solutions, suspensions, and emulsions.

Pharmaceutically acceptable excipients are well known in the art and include diluents, fillers, binders, lubricants, disintegrants, glidants, colorants, pigments, taste masking agents, sweeteners, plasticizers, and any acceptable auxiliary substances such as absorption enhancers, penetration enhancers, surfactants, co-surfactants, and specialized oils. The proper excipient(s) are selected based in part on the dosage form, the intended mode of administration, the intended release rate, and manufacturing reliability. Examples of common types of excipients include various polymers, waxes, calcium phosphates, and sugars. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; and polyacrylic acids including their copolymers and crosslinked polymers thereof, i.e. Carbopol® (B.F. Goodrich), Eudragit® (Rohm), polycarbophil and chitosan polymers. Waxes include white beeswax, microcrystalline wax, carnauba wax, hydrogenated castor oil, glyceryl behenate, glycerylpalmito stearate, saturated polyglycolyzed glycerate. Calcium phosphates include dibasic calcium phosphate, anhydrous dibasic calcium phosphate, and tribasic calcium phosphate. Sugars include simple sugars such as lactose, maltose, mannitol, fructose, sorbitol, sacarose, xylitol, isomaltose, and glucose as well as complex sugars (polysaccharides) such as maltodextrin, amylodextrin, starches including maize, and modified starches.

For liquid dosage forms, such as parenteral formulations, water is commonly used as a main excipient although other pharmacologically compatible liquids can be employed as well.

Any form of benzene sulfonic acid salt of pramipexole can be used in the pharmaceutical composition. Preferred salts are the pramipexole besylate forms, especially crystalline (S)-pramipexole besylate anhydrate, but other salt forms including dibesylate and/or hydrated forms are also included. Preferably the benzene sulfonic acid salt of pramipexole is in particulate form having an average particle size of 200 microns or less, typically having an average particle size of 0.1 to 100 microns, more typically 1 to 50 microns. The amount of pramipexole salt contained in a unit dosage form is an amount effective to treat one or more pramipexole-treatable diseases or conditions as is hereinafter defined and can be determined by workers skilled in the art without undue experimentation. Generally this amount ranges from 0.05 to 10 mg, more typically from 0.1 to 5 mg of the pramipexole salt.

As mentioned above, oral dosage forms are preferred and include tablets, capsules, sachets/granules, and powders. Tablets can be soluble tablets, dispersible tablets, effervescent tablets, chewable tablets, lyophilized tablets, coated tablets including sugar coatings, enteric coatings, and gastro-soluble coatings, and modified release tablets including microencapsulated active substance tablets, matrix tablets, and coated tablets such as polymer coated extended release tablets and osmotic tablets of the mono-compartmental or bi-compartmental type. Capsules include hard gelatin capsules that can be filled with powder, pellets, granules, small tablets or mini-tablets. The capsule and/or the material placed within can be coated such as for enteric release or modified release. Soft capsules are also included and are more typically filled with liquids or dispersions, but are not limited thereto. Sachets or granules can be effervescent granules, coated granules, enteric granules, or modified release granules.

One embodiment of the present invention relates to an immediate release tablet. An "immediate release" as used herein means that at least 80% of the pramipexole salt in the tablet is dissolved by 30 minutes under a dissolution test using USP Apparatus 1 (basket) at 100 rpm in purified water at 37° C. Any conventional immediate release composition can be used in formulating the pramipexole salt immediate release tablet. Typically such tablets contain one or more binders and/or diluents such as HPMC, microcrystalline cellulose, a calcium phosphate, lactose, and mannitol; a lubricant such as magnesium stearate; and optionally a disintegrant such as sodium starch glycollate, crosscarmellose or crosspovidone. Additional excipients such as colorants, antioxidants, etc can also be present. In one embodiment, the pharmaceutical composition comprises, as excipients, mannitol, maize starch, and povidone. Sample compositions of tablets for oral administration of pramipexole are as follows:

| Pramipexole (as base) | 0.088 mg | 0.18 mg | 0.7 mg | 0.88 mg |
|---|---|---|---|---|
| Mannitol | 49.455 mg | 61.0 mg | 121.50 mg | 162.0 mg |
| Magnesium stearate | 1.230 mg | 1.50 mg | 3.0 mg | 4.0 mg |
| Maize starch | 25.010 mg | 30.90 mg | 61.85 mg | 82.55 mg |
| Maize starch | 7.300 mg | 9.0 mg | 18.00 mg | 24.0 mg |
| Colloidal silicon dioxide | 0.940 mg | 1.20 mg | 2.30 mg | 3.10 mg |
| Povidone | 0.940 mg | 1.15 mg | 2.35 mg | 3.10 mg |

All of the pharmaceutical compositions can be made by conventional techniques. Generally, the formulating involves combining the pramipexole salt with one or more excipients. For making tablets, wet granulation, dry granulation and direct compression techniques are suitable. Similarly, wet granulation, dry granulation, pellitization, and powder blending are all possible techniques for making a pharmaceutical composition that can be filled into a unit dosage capsule.

Benzene sulfonic acid salts of pramipexole, especially pramipexole besylate are useful in treatment of, and the preparation of medicaments for treatment of, any pramipexole-treatable disease or condition. Such diseases or conditions are typically those which would be benefited by dopamine modulation. Specifically preferred diseases and conditions include schizophrenia, Parkinson's disease, Parkinsonism, hypertension, and various forms of depression. It may be used alone or in combination with ergot preparation (e.g. bromocryptine or pergolide) or with levodopa. The treatment comprises administering an effective amount of the pramipexole salt, generally as a pharmaceutical composition as described above, to a patient in need thereof. The patient is an animal, usually a mammal, including humans. The effective amount is generally within the range of 0.1 to 10 mg for a human or approximately 0.0005 to 0.06 mg/kg of body weight. The dose is usually administered 1 to 4 four times per day in one or two unit doses per administration.

The present invention is more particularly described and explained by the following examples, wherein substantially optically pure (S)-pramipexole was used throughout. It is to be understood, however, that the present invention is not limited to these examples and various changes and modifications may be made without departing from the scope of the present invention.

Preparation 1

Pramipexole base by neutralization of pramipexole dihydrochloride.

45 g of pramipexole dihydrochloride was dissolved in 250 ml of water. Then, a solution of 15.8 g of NaOH in 100 ml of water was added slowly. The emulsion was extracted four times with 100 ml of chloroform. The combined chloroform layers were washed with brine, dried with sodium sulfate and the solvent was evaporated.

Yield: 32 g, m.p. 126-128° C.

EXAMPLE 1

Pramipexole Besylate 2.11 g of pramipexole was dissolved in 20 ml of methanol under heating. A solution of 1.58 g of benzene sulfonic acid in 10 ml of hot methanol was added in one portion. After standing at room temperature for 15 minutes, crystallization started. The flask was left at room temperature overnight. The solid was filtered off, washed with heptane and dried at 40° C. under vacuum.

Yield: 2.64 g. NMR: confirmed the structure of pramipexole besylate (1:1). m.p. 243-246° C. Solubility in water: approx. 20 mg/ml. Optical rotation $[\alpha]=-52.84°$.

The optical rotation was determined as follows. 260.5 mg of the solid was dissolved in 25 ml of methanol. The flask was shaken until a clear solution resulted, then the optical rotation was measured with a Perkin Elmer 243 polarimeter. Results: $\alpha=-0.551$ (c=1.042, methanol); $[\alpha]=-52.84°$

EXAMPLE 2

Pramipexole Besylate 4.22 g of pramipexole was dissolved in 40 ml of methanol while heating. Then a solution of 3.16 g of benzene sulfonic acid dissolved in 20 ml of hot methanol was added in one portion. After standing at room temperature for 15 minutes crystallization started, ~10 minutes later the complete content of the flask solidified. The flask was left at room temperature over night. The solid was filtered off, dried at 40° C. under vacuum. Yield: 5.38 g (73%)

NMR: the 1:1 salt was isolated. Optical rotation [α]=−52.15°

The optical rotation was determined by the same procedure as described above and yielded α=−0.525 (c=1.007, methanol); [α]=−52.15°.

EXAMPLE 3

Hygroscopicity of Pramipexole Dihydrochloride Monohydrate

The hygroscopicity was measured using a Dynamic Vapor Sorption apparatus or DVS (Surface Measurement Systems Ltd, UK) at 25° C. and at various controlled relative humidity conditions from 0 to 90%. At 60% relative humidity the sample exhibits a water uptake of over 1.2% relative to dry mass. In the step from 70% and 80% relative humidity the total water uptake is 5% relative to the dry mass.

EXAMPLE 4

Hygroscopicity of Pramipexole Besylate 32.57 mg of pramipexole besylate anhydrate was transferred into a sample crucible of the DVS system and placed in the humidity chamber at 25° C. First the relative humidity was changed from 0% to 60% and back to 0% (cycle 1). Subsequently, the relative humidity was raised by steps of 10% until 90% and reduced with steps of 10% until 0% (cycle 2). Finally, the relative humidity was changed to 60% and back to 0% (cycle 3). At each step the sample was conditioned till constant weight.

The pramipexole besylate shows a minimal uptake of water resulting from the increase in relative humidity (<0.1%). During the drying step of the first cycle (RH 0%), the mass almost regains the initial value. However, after the drying steps of the second and third cycle, a small amount of water is left (approximately 0.025%).

Each of the patents and publications mentioned above is incorporated herein in its entirety. The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A crystalline benzene sulfonic acid salt of pramipexole, which has an optical purity of at least 98%.

2. The salt according to claim 1, which is in an isolated state

3. The salt according to claim 1, wherein said salt is solvent-free

4. The salt according to claim 1, wherein said salt is anhydrous.

5. The salt according to claim 4, wherein the ratio of benzene sulfonic acid moiety to pramipexole moiety is about 1:1.

6. The salt according to claim 1, which is an (S)-pramipexole salt.

7. The salt according to claim 1, which is predominantly (S)-pramipexole salt and having an optical rotation of −49° or less in methanol.

8. The salt according to claim 7, having an optical rotation of −52° or less in methanol.

9. A pharmaceutical composition comprising a benzene sulfonic acid salt of pramipexole and a pharmaceutically acceptable excipient.

10. The pharmaceutical composition according to claim 9, wherein said pramipexole salt has an optical purity of at least 95%.

11. The pharmaceutical composition according to claim 10, wherein said pramipexole salt is an (S)-pramipexole salt having an optical purity of at least 98%.

12. The pharmaceutical composition according to claim 9, wherein said composition is a solid dosage form.

13. The pharmaceutical composition according to claim 12, wherein said pramipexole salt is crystalline.

14. The pharmaceutical composition according to claim 12, wherein said solid dosage form is an oral dosage form.

15. The pharmaceutical composition according to claim 14, wherein said benzene sulfonic acid salt of pramipexole is contained in said dosage form in an amount within the range of 0.1 to 10 mg.

16. The pharmaceutical composition according to claim 9, wherein said pramipexole salt is (S)-pramipexole besylate.

17. The pharmaceutical composition according to claim 16, wherein said pramipexole salt is crystalline (S)-pramipexole besylate.

18. The pharmaceutical composition according to claim 16, wherein said composition is a solid dosage form.

19. The pharmaceutical composition according to claim 18, wherein said solid dosage form is an oral dosage form.

20. The pharmaceutical composition according to claim 19, wherein said (S)-pramipexole besylate is contained in said dosage form in an amount within the range of 0.1 to 10 mg.

* * * * *